Figure 1:
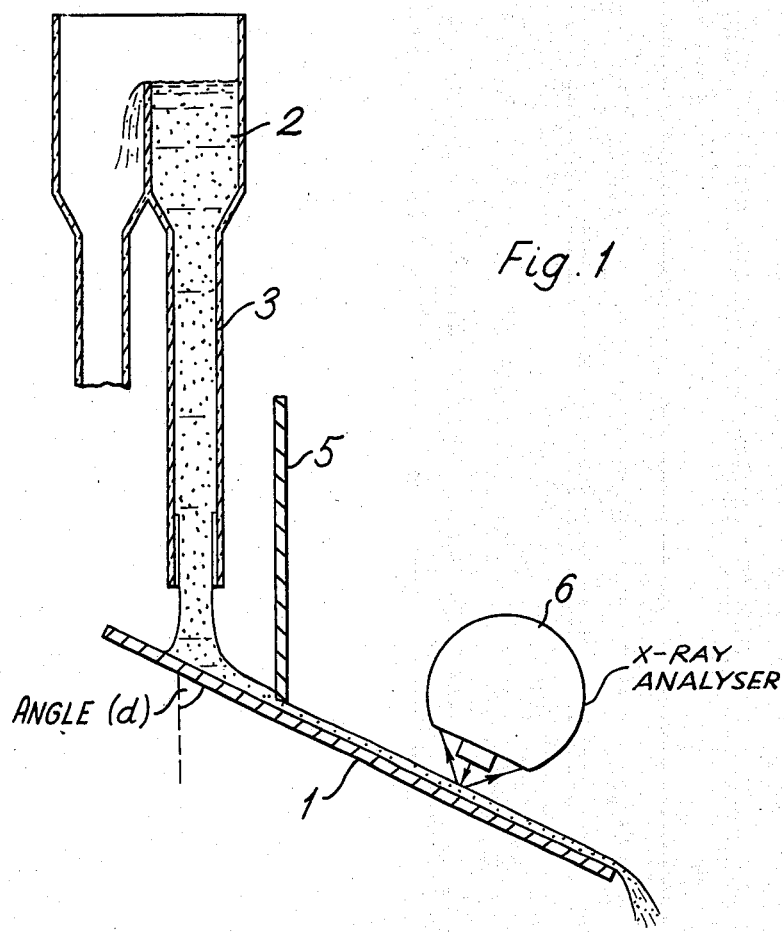

United States Patent [19]
Carr-Brion et al.

[11] 3,980,882
[45] Sept. 14, 1976

[54] METHODS AND APPARATUS FOR THE CHEMICAL ANALYSIS OF FLOWING MATERIALS

[75] Inventors: Kenneth Garfield Carr-Brion, Broom; Angela Wendy Williams, Knebworth, both of England

[73] Assignee: National Research Development Corporation, London, England

[22] Filed: Apr. 18, 1974

[21] Appl. No.: 462,077

[30] Foreign Application Priority Data
May 16, 1973 United Kingdom............... 23300/73

[52] U.S. Cl.............................. 250/272; 250/277 R; 250/358 R
[51] Int. Cl.²....................................... G01N 23/20
[58] Field of Search ........... 250/272, 273, 358, 359, 250/360, 277

[56] References Cited
UNITED STATES PATENTS

| | | | |
|---|---|---|---|
| 2,971,461 | 2/1961 | Bradford et al..................... | 250/359 |
| 3,012,140 | 12/1961 | Pellissier et al..................... | 250/272 |
| 3,612,859 | 10/1971 | Schumacher ....................... | 250/272 |
| 3,710,104 | 1/1973 | Pavlik ................................. | 250/272 |
| 3,787,691 | 1/1974 | Laurer ................................ | 250/272 |

*Primary Examiner*—Davis L. Willis
*Attorney, Agent, or Firm*—Cushman, Darby & Cushman

[57] ABSTRACT

The present invention concerns apparatus for analyzing flowable substances such as slurries using techniques such as X-ray fluorescence, infra-red reflectance or emisson spectrography. The material to be analyzed is caused to flow over a plate in a very thin film so that a quantitive measurement of the elements of interest in the material can be made by analytical systems.

5 Claims, 3 Drawing Figures

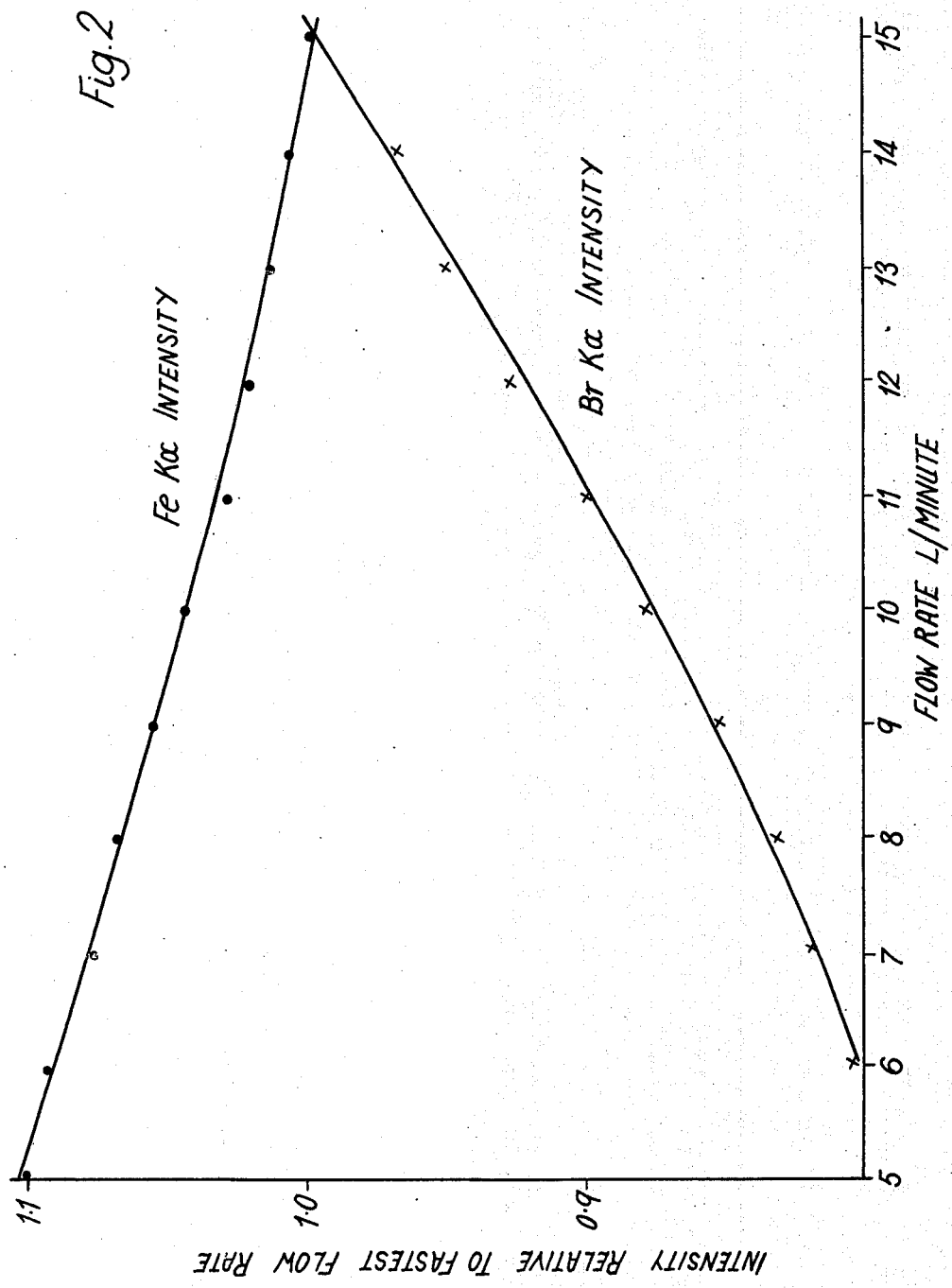

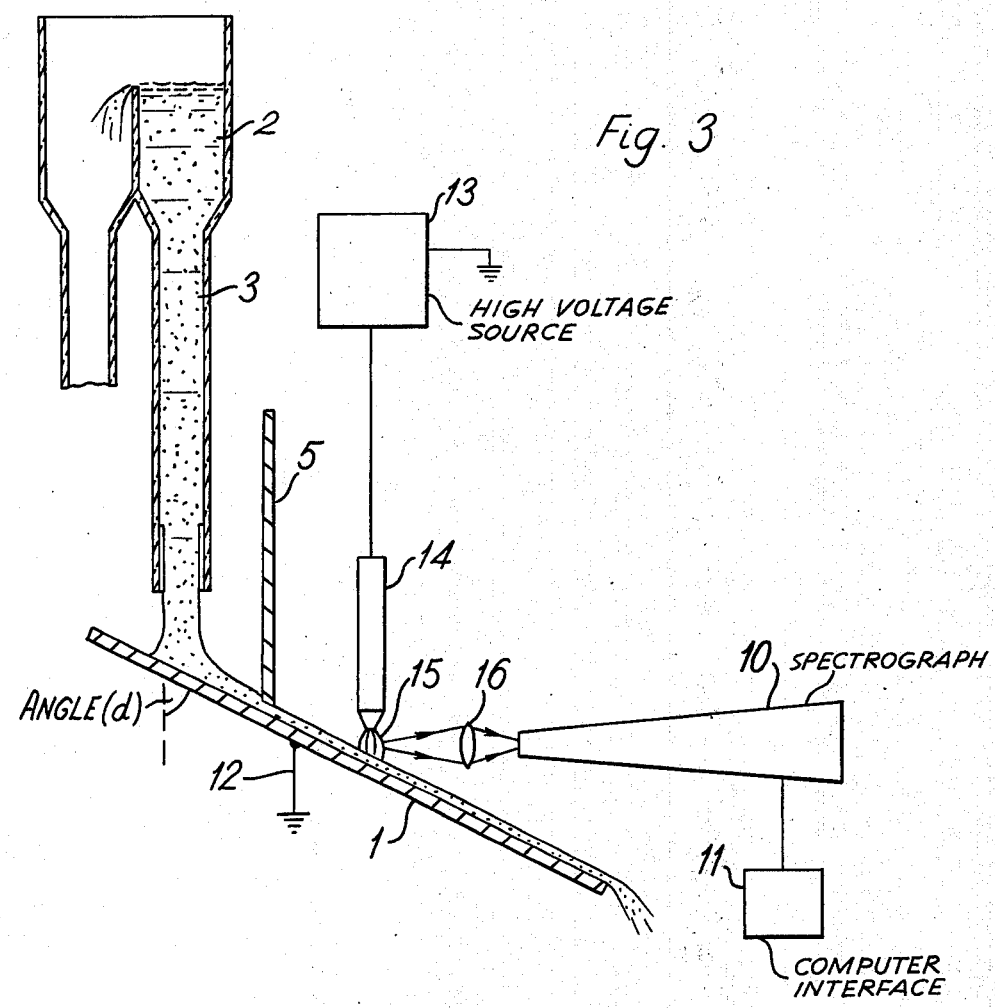

METHODS AND APPARATUS FOR THE CHEMICAL ANALYSIS OF FLOWING MATERIALS

The present invention concerns a method and apparatus for analysing flowable substances such as slurries.

It is particularly concerned with analytical techniques using either x-ray fluorescence, infra-red reflectance or emission spectrography. Such techniques will hereinafter be referred to as being of the kind specified.

When using techniques of the kind specified it is important for the sample to have a surface at a constant distance from the analytical system.

It is current practice to achieve these conditions in part by the use of a sample cell having a window between the flowing sample and the analytical system or by the use of a jet of flowing sample. With both these solutions it is difficult to obtain a very thin layer of flowing sample which is stable enough to make quantitative measurements by transmission through it or to design a thin enough cell or jet which is not liable to have coarse particles lodge in it. In addition, with a jet an automatic shutter mechanism is required to isolate the analytical system from the jet during start up or stopping, since splashing of the analytical system can occur under these conditions.

In accordance with one aspect of the present invention there is provided a method of analysing flowable materials comprising arranging the material to flow over a flat or slightly curved surface with a thickness which is substantially within predetermined levels and an analytical system employing a technique of the kind specified mounted a predetermined distance from said surface.

According to another aspect of the present invention there is provided apparatus for analysing flowable materials comprising a flat or slightly curved surface, means for causing the material to be analysed to flow over said surface with a predetermined thickness, and an analysing system employing a technique of the kind specified mounted a predetermined distance from said surface.

An embodiment of the present invention will now be described by way of example and with reference to the accompanying drawings in which:

FIG. 1 is a diagrammatic view of apparatus for analysing flowable materials constructed in accordance with the present invention, and FIG. 2 is a graph showing typical results from a device similar to that shown in FIG. 1, and FIG. 3 shows apparatus constructed in accordance with the present invention for use in emission spectrography.

The apparatus shown in FIG. 1 comprises a plate 1 having a flat or slightly curved surface over which a liquid or slurry to be analysed is arranged to flow in the form of a film of controllable thickness. The liquid or slurry is fed from a constant head tank 2 to ensure an approximately stable flow rate to a discharge pipe 3, the discharge pipe 3 being made of any suitable material resistant to corrosion or abrasion. The stream of liquid or slurry hits the plate 1 inclined to the discharge flow and spreads to form a layer. The angle ($d$) of the plate 1 to the discharge flow depends on the properties of the liquid or slurry, its flow rate and desired sample depth. However, it is essential that the thickness of the material flowing over the plate 1 should not exceed 1 millimeter under any circumstances. Thus suitable means may be provided for altering the angle of the plate 1 in accordance with requirements. A splash guard 5 ensures that an analytical system 6 is not splashed by the liquid or slurry. In the present embodiment the analytical system is a non-dispersive x-ray analyser of known kind. The plate 1 over which the samples flow can be made from any suitable corrosive or abrasive resistant material and may incorporate suitable elements for transmission measurements with x-ray fluorescence or x-ray absorption techniques. It may also be conductive and act as an earth for the discharge used in emission spectrography, and such an embodiment is described with reference to FIG. 3.

Results obtained from such a device as shown in FIG. 1 and fed with a solution of lithium bromide are shown in FIG. 2. This is a plot of x-ray fluorescent intensity from the liquid sample (Br K x-rays) and transmitted x-ray intensity from the stainless steel plate (Fe K x-rays). Precision of measurement of the fluorescent intensity was 0.3% and transmitted intensity 0.3% expressed as one coefficient of variation. The increase in Br K intensity and corresponding decrease in Fe K intensity is due to the increasing thickness of the film of solution as the flow rate is increased.

Although the device described above uses an x-ray analyser its basic construction is of course equally applicable to analytical systems using x-ray fluorescence, infra-red reflectance and emission spectrography, and a device using the latter principle will now be described with reference to FIG. 3, in which integers similar to FIG. 1 are given the same reference numerals.

However, the analytical system in the embodiment of FIG. 3 comprises a direct reading spectrograph 10 having a computer interface generally indicated at 11 for direct readout. The plate 1 is made of conducting material and is earthed at 12 whilst a high voltage exciting source 13 provides a sufficiently high voltage at an electrode 14 to generate a discharge at 15 on the surface of the substance to be analysed. Light from this discharge is focused into the spectrograph 10 by a lens system generally indicated at 16. Thus the discharge passes through the film of the substance to be analysed and a fraction of the film disturbed by the discharge would continuously pass into the discharge, be excited and emit characteristic visible, near infra-red or ultra violet radiation. The plate may be of any suitable conducting metal such as copper or graphite.

The spectrograph 10 is of known kind and preferably employs an optical grating which splits the incoming radiation into its spectrum. Associated with the grating are a number of slits each being positioned to pass a particular line. A photomultiplier or other radiation detecting device is positioned behind each slit and the outputs of the photomultipliers are taken to the computer interface 11. Alternatively, the photomultiplier outputs could be taken to a CRT for display in the usual manner.

Reverting to the device described with reference to FIG. 1, when used in transmission measurements for x-ray fluorescence the material of the plate 1 will contain an element for example, iron, which is made to fluoresce by passing x-rays from a tube or radio isotope source through the film of the substance to be analysed, the absorption of the iron x-ray being measured after they have passed back through the film. Thus the fluorescence x-rays measured depend on the sum of the absorbing power of the film for both exciting and fluorescent x-rays. It is also possible to have part of the plate 1 made of x-ray transmitting material such as polypropylene. In such a case the x-ray source and the detector would be placed on either side of the film. Naturally, it is immaterial which is above and which is below the film.

In an embodiment of the present invention employing an infrared reflectance technique, the analytical system would comprise an infra-red light source for illuminating the material being analysed together with a detector well known in the art for detecting infra-red radiation which has passed through the material. Associated with the detector are filters determining which radiation frequencies reach the detector. Thus certain compounds absorb certain frequencies and the variations in intensity in these freqencies caused by selective absorption can be measured by the outputs of the detectors. An example of this is the measurement of the presence of water in ethanol with the water tending to absorb in the 3 micron waveband. In order to reduce the effect of varying ambient conditions the radiation intensity of a frequency to the side of the waveband of interest is also measured and the two intensities ratioed in a well known manner. This may be achieved by using a single detector and having a pair of filters mounted so that they can be rotated successively into the path of the detected radiation.

We claim:

1. An apparatus for use in the analytical determination of a given substance in a flowing material, said apparatus comprising:

a member having an upwardly facing substantially planar surface;

means for causing a stream of said material to flow in a substantially invariant manner over said surface in the form of a thin film; and an analytical system comprising means selectively responsive to electromagnetic radiation of at least one wavelength which corresponds to a spectral characteristic of said given substance, said selectively responsive means being disposed in fixed relationship to said surface out of contact with said film for receiving radiation travelling from the vicinity of a given portion of said film.

2. An apparatus according to claim 1, in which at least part of said member consists of electrically conductive material which extends to a portion of said surface over which said stream flows, and the apparatus further comprises an electrode disposed above said member so that an electrical discharge can be caused to pass between said electrode and said portion of said surface, said selectively responsive means being an optical spectrograph disposed to receive light emitted from said electrical discharge.

3. An apparatus according to claim 1, in which said analytical system further comprises an x-ray source disposed for irradiating said portion of said film, and said selectively responsive means is operative so that said at least one wavelength is a wavelength of fluorescent x-rays of said given substance excited by radiation from said source.

4. An apparatus according to claim 1, in which said means for causing said stream to flow over said surface comprises means, disposed in fixed relationship to said surface, for discharging substantially vertically onto said surface a stream of said material having a substantially constant flow rate.

5. An apparatus according to claim 1, in which said means for causing said stream to flow over said surface is operative so that the thickness of said film does not exceed 1 millimeter.

* * * * *